(12) United States Patent
Volk et al.

(10) Patent No.: US 6,897,322 B2
(45) Date of Patent: May 24, 2005

(54) METHOD OF PRODUCING 1-ALKYL-3-ARYL-5-DIFLUOROMETHOXY-1H-PYRAZOLES

(75) Inventors: Thorsten Volk, Mannheim (DE); Michael Puhl, Lampertheim (DE); Cyrill Zagar, Mannheim (DE); Rene Lochtman, Mannheim (DE); Norbert Götz, Worms (DE); Gerhard Hamprecht, Weinheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/250,503

(22) PCT Filed: Jan. 15, 2002

(86) PCT No.: PCT/EP02/00347
§ 371 (c)(1),
(2), (4) Date: Jul. 3, 2003

(87) PCT Pub. No.: WO02/055504
PCT Pub. Date: Jul. 18, 2002

(65) Prior Publication Data
US 2004/0059128 A1 Mar. 25, 2004

(30) Foreign Application Priority Data
Jan. 16, 2001 (DE) .......................... 101 01 762

(51) Int. Cl.⁷ ............................................ C07D 231/14
(52) U.S. Cl. ................................................... 548/366.1
(58) Field of Search ........................ 548/366.1; 514/407

(56) References Cited
FOREIGN PATENT DOCUMENTS

| EP | 361 114 | 4/1990 |
| EP | 443 059 | 8/1991 |
| JP | 0443059 A1 * | 2/1990 |
| WO | WO95/19967 * | 1/1995 |

OTHER PUBLICATIONS

Auwers,J.Prakt.Chem.,vol. 110,1925, 204–234.
Chem. Soc.of Japan, Bull.Chem.Soc.,vol. 54,3221–3222(1981) Kagaruki et al.
J.Prakt.Chem.vol. 52, 1895,23–57, Rothenburg.
Justus LiebigsAnn.Chem.vol. 352, 1907,163–193 Michaelis.
91–136056 Derwent Abst.
92–320741 Derwent Abst.
94–269416 Derwent Abst.
98–019962 Derwent Abst.

* cited by examiner

Primary Examiner—Joseph K. McKane
Assistant Examiner—Robin Waller
(74) Attorney, Agent, or Firm—Novak Druce & Quigg, LLP

(57) ABSTRACT

The invention relates to a method of preparing 1-alkyl-3-aryl-5-difluoromethoxy-1H-pyrazoles of the formula (I), wherein aryl represents a mono- or polysubstituted phenyl ring, and $R^1$ represents $C_1$–$C_4$ alkyl. The inventive method is characterized by reacting, in a first reaction step, a β-ketoester of the general formula (II) with hydrazine and by successively reacting the reaction product obtained with chlorodifluoromethane and a compound $R^1$-L, wherein $R^1$ has the meanings indicated above and L represents the leaving group of a nucleophilic displacement reaction.

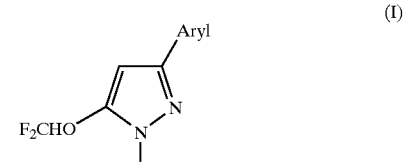

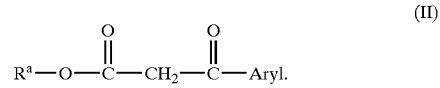

11 Claims, No Drawings

METHOD OF PRODUCING 1-ALKYL-3-ARYL-5-DIFLUOROMETHOXY-1H-PYRAZOLES

The present invention relates to a process for preparing 1-alkyl-3-aryl-5-difluoromethoxy-1H-pyrazoles of the formula I

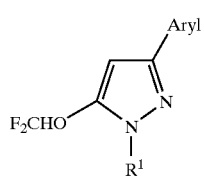

in which Aryl is a mono- or polysubstituted phenyl ring and $R^1$ is $C_1$–$C_4$-alkyl.

1-Alkyl-3-aryl-5-difluoromethoxy-1H-pyrazoles of the formula I are important herbicides. In the prior art, they have hitherto been prepared in a synthesis which comprises the following steps:

1. reaction of 3-aryl-3-oxopropionic esters II (hereinbelow also referred to as β-keto esters II)

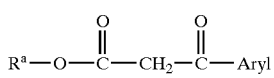

in which $R^a$ is, for example, $C_1$–$C_4$-alkyl, and aryl has the meanings given above, with alkylhydrazines and
2. reaction of the resulting 3-aryl-5-hydroxy-1H-pyrazole substituted by alkyl on the pyrazole nitrogen with a halodifluoromethane.

These processes are described, for example, in EP-A 443059, EP-A 361114, JP 03072460, JP 04225937 and JP 06199804.

This procedure has two grave disadvantages. Firstly, for step 1, highly expensive alkylhydrazines have to be used. Secondly, in the reaction of II with alkylhydrazine, in addition to the desired 1-alkyl-3-aryl-5-hydroxy-1H-pyrazoles IV, considerable amounts of the isomers V are formed.

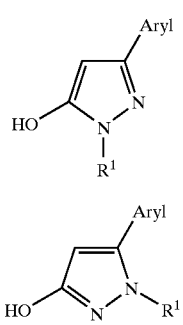

In general, the ratio of desired product IV to the undesired isomer V is only 3:1 or less. Moreover, the cyclization yields in step 1, based on the expensive alkylhydrazine employed, are low. Furthermore, owing to their similar physical properties, the separation of the hydroxypyrazole isomers IV and V is very complicated. The separation of the reaction products of the isomer mixture IV+V with halodifluoromethane (step 2) is likewise unfavorable, since V, in contrast to IV, has a strong tendency to form N-difluoromethylpyrazolones which give rise to further problems during the work-up of the target product I.

It is an object of the present invention to provide a process for preparing the 1-alkyl-3-aryl-5-difluoromethoxy-1H-pyrazoles I defined at the outset, which process avoids the use of alkylhydrazine and which affords the compound I in good, but at least comparable, total yields.

Surprisingly, it has been found that the 3-aryl-5-hydroxy-1H-pyrazoles III or their tautomers, the 3-arylpyrazol-5-ones of the formula IIIa,

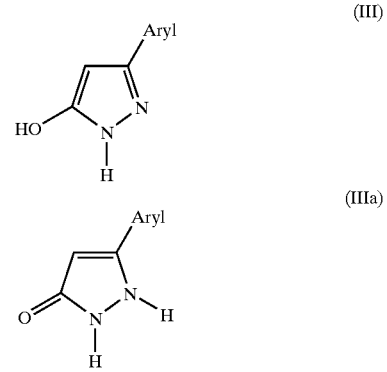

which can be obtained in good yields by reacting 3-aryl-3-ketopropionic esters II with hydrazine, can be converted with high selectivity by reaction with alkylating agents into the 1-alkyl-3-aryl-5-hydroxy-1H-pyrazoles IV, and that it is furthermore possible, by reacting the compounds III or IIIa with chlorodifluoromethane, to prepare, with good selectivities, the difluoromethoxypyrazoles of the formula VI

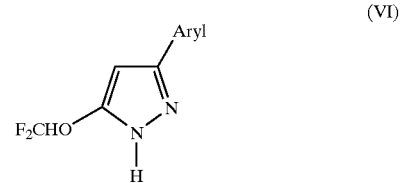

which for their part can be converted selectively and with good yields by reaction with alkylating agents into the 1-alkyl-3-aryl-5-difluoromethoxy-1H-pyrazoles I.

Accordingly, the invention relates to a process for preparing 1-alkyl-3-aryl-5-difluoromethoxy-1H-pyrazoles of the formula I defined at the outset, which process comprises reacting, in a first reaction step, a β-keto ester of the formula II with hydrazine, giving a hydroxypyrazole of the formula III, which is subsequently, in a second and third reaction step, reacted successively with chlorodifluoromethane and a compound $R^1$-L, where $R^1$ has the meanings given above and L is a nucleophilically displaceable leaving group. Here, it is possible to initially react the hydroxypyrazole III obtained in step 1 with a compound $R^1$-L and then react the resulting 1-alkylated hydroxypyrazole IV, if appropriate as a mixture with its isomer V, with chlorodifluoromethane (hereinbelow referred to as variant A). It is also possible to initially react III with chlorodifluoromethane and, to prepare the compound I, to react the resulting difluoromethoxypyrazole VI with a compound $R^1$-L (hereinbelow referred to as variant B).

Nucleophilically displaceable leaving groups L are, in principle, understood as meaning all groups which are known to be displaceable under the conditions of an alkylation of amines by the nucleophilic N-atom. These include, in particular, the halogen atoms chlorine, bromine and iodine, alkyl- and arylsulfonate groups, for example phenylsulfonate, tolylsulfonate (tosylate) and mesylate, carboxylate groups, such as acetate, furthermore alkyl sulfate groups, such as methyl sulfate and ethyl sulfate, and also dialkyloxonium groups, such as the dimethyloxonium group or diethyloxonium group in Meerwein salts. Preferred groups L are iodine, bromine, chlorine and the groups $OSO_2$—$OR^1$ and $[O(R^1)_2]\oplus$. Particular preference is given to the group $OSO_2$—$OR^1$, in particular if $R^1$ is a methyl group.

Examples of other meanings are:

$C_1$–$C_4$-alkyl: for example methyl, ethyl, propyl, 1-methylethyl, butyl, 1-methylpropyl, 2-methylpropyl or 1,1-dimethylethyl;

$C_1$–$C_6$-alkyl: $C_1$–$C_4$-alkyl as mentioned above, and also, for example, n-pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl or 1-ethyl-3-methylpropyl;

$C_1$–$C_4$-alkoxy and the alkoxy moieties of $C_1$–$C_4$-alkoxy-$C_1$–$C_4$-alkyl and $C_1$–$C_4$-alkoxycarbonyl-$C_1$–$C_4$-alkyl: for example methoxy, ethoxy, propoxy, 1-methylethoxy, butoxy, 1-methylpropoxy, 2-methylpropoxy or 1,1-dimethylethoxy;

$C_1$–$C_4$-alkoxy-$C_1$–$C_4$-alkyl: $C_1$–$C_4$-alkyl which is substituted by $C_1$–$C_4$-alkoxy as mentioned above, i.e., for example, methoxymethyl, ethoxymethyl, propoxymethyl, (1-methylethoxy)methyl, butoxymethyl, (1-methylpropoxy)methyl, (2-methylpropoxy)methyl, (1,1-dimethylethoxy)methyl, 2-(methoxy)ethyl, 2-(ethoxy)ethyl, 2-(propoxy)ethyl, 2-(1-methylethoxy)ethyl, 2-(butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(propoxy)propyl, 2-(1-methylethoxy)propyl, 2-(butoxy)propyl, 2-(1-methylpropoxy)propyl, 2-(2-methylpropoxy)propyl, 2-(1,1-dimethylethoxy)propyl, 2-(methoxy)butyl, 2-(ethoxy)butyl, 2-(propoxy)butyl, 2-(1-methylethoxy)butyl, 2-(butoxy)butyl, 2-(1-methylpropoxy)butyl, 2-(2-methylpropoxy)butyl, 2-(1,1-dimethylethoxy)butyl;

$C_1$–$C_4$-alkoxycarbonyl-$C_1$–$C_4$-alkyl: $C_1$–$C_4$-alkyl which is substituted by $C_1$–$C_4$-alkoxycarbonyl, i.e., for example, methoxycarbonylmethyl, ethoxycarbonylmethyl, propoxycarbonylmethyl, (1-methylethoxy)carbonylmethyl, butoxycarbonylmethyl, (1-methylpropoxy)carbonylmethyl, (2-methylpropoxy)carbonylmethyl, (1,1-dimethylethoxy)carbonylmethyl, 2-(methoxycarbonyl)ethyl, 2-(ethoxycarbonyl)ethyl, 2-(propoxycarbonyl)ethyl, 2-(1-methylethoxycarbonyl)ethyl, 2-(butoxycarbonyl)ethyl, 2-(1-methylpropoxycarbonyl)ethyl, 2-(2-methylpropoxycarbonyl)ethyl, 2-(1,1-dimethylethoxycarbonyl)ethyl, 2-(methoxycarbonyl)propyl, 2-(ethoxycarbonyl)propyl, 2-(propoxycarbonyl)propyl, 2-(1-methylethoxycarbonyl)propyl, 2-(butoxycarbonyl)propyl, 2-(1-methylpropoxycarbonyl)propyl, 2-(2-methylpropoxycarbonyl)propyl, 2-(1,1-dimethylethoxycarbonyl)propyl, 2-(methoxycarbonyl)butyl, 2-(ethoxycarbonyl)butyl, 2-(propoxycarbonyl)butyl, 2-(1-methylethoxycarbonyl)butyl, 2-(butoxycarbonyl)butyl, 2-(1-methylpropoxycarbonyl)butyl, 2-(2-methylpropoxycarbonyl)butyl, 2-(1,1-dimethylethoxycarbonyl)butyl;

$C_1$–$C_6$-alkylcarbonyl: for example acetyl, propionyl, n-butyryl, isobutyryl, pivaloyl, n-hexenoyl;

$C_2$–$C_6$-alkenyl: for example ethenyl, prop-1-en-3-yl, but-1-en-4-yl, 1-methylprop-2-en-1-yl, 2-methylprop-2-en-1-yl, 2-buten-1-yl, 1-penten-3-yl, 1-penten-4-yl, 2-penten-4-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-2-en-1-yl, 1-ethylprop-2-en-1-yl, hex-3-en-1-yl, hex-4-en-1-yl, hex-5-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-2-en-1-yl, 1,2-dimethylbut-3-en-1-yl, 1,3-dimethylbut-2-en-1-yl, 1,3-dimethylbut-3-en-1-yl, 2,2-dimethylbut-3-en-1-yl, 2,3-dimethylbut-2-en-1-yl, 2,3-dimethylbut-3-en-1-yl, 3,3-dimethylbut-2-en-1-yl, 1-ethylbut-2-en-1-yl, 1-ethylbut-3-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl or 1-ethyl-2-methylprop-2-en-1-yl;

$C_2$–$C_6$-alkynyl: for example ethynyl, propargyl, but-1-yn-3-yl, but-1-yn-4-yl, but-2-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methylbut-1-yn-3-yl, 3-methylbut-1-yn-4-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-3-yl, 3-methylpent-1-yn-4-yl, 3-methylpent-1-yn-5-yl, 4-methylpent-2-yn-4-yl or 4-methylpent-2-yn-5-yl.

Suitable substituents for aryl are, in principle, all atoms or atom groups which are inert under the reaction conditions and which are in particular unreactive with respect to alkylating agents $R^1$-L and halodifluoromethanes. Here, it is also possible for 2 substituents attached to adjacent carbon atoms to form a 3-, 4- or 5-membered saturated or unsaturated chain. The chain may also comprise, as chain members, one or two heteroatoms, for example nitrogen, sulfur or oxygen, and/or one or two carbonyl or thiocarbonyl functions. Examples of suitable substituents are halogen, $C_1$–$C_4$-alkyl, which may additionally be substituted by halogen, phenyl, a $C_1$–$C_4$-alkoxy group, a $C_1$–$C_4$-alkoxycarbonyl group or a $C_1$–$C_4$-alkylcarbonyloxy group, $C_2$–$C_6$-alkenyl, $C_2$–$C_6$-alkynyl, $NO_2$, $COOR^5$, $OR^6$, $C(O)R^7$, $SO_nR^8$ and $SO_nNR^9R^{10}$, where $R^5$, $R^6$, $R^7$, $R^8$, $R^9$ and $R^{10}$ independently of one another are selected from the group consisting of hydrogen, $C_1$–$C_4$-alkyl, $C_3$–$C_4$-alkenyl, $C_3$–$C_4$-alkynyl, $C_1$–$C_4$-alkoxy-$C_1$–$C_4$-alkyl and $C_1$–$C_4$-alkoxycarbonyl-$C_1$–$C_4$-alkyl and where n is 0, 1 or 2, furthermore NH(CO—$R^{12}$) and N(CO—$R^{12}$)$_2$, where $R^{12}$ has one of the meanings mentioned for $R^6$ and is in particular $C_1$–$C_4$-alkyl. Examples of chains are 1,3-propylene, 1,4-butylene, 1,3-dioxypropylene, 1-oxy-1,4-butylene and the like.

All reactions described here are carried out in reaction vessels which are customary for such reactions, it being possible to carry out the reaction either continuously or batchwise. In general, the reaction in question is carried out under atmospheric pressure. In the case of low-boiling solvents, it is also possible to carry out the reaction in question under superatmospheric pressure.

The preparation of the 3-aryl-5-hydroxypyrazoles III in step 1 of the process according to the invention is carried out similarly to the preparation of N-substituted pyrazolones or hydroxypyrazolones starting from β-keto esters of the formula II, where, in contrast to the prior art, the β-keto ester II is not reacted with an alkylhydrazine but with hydrazine, either in pure form or as hydrazine hydrate.

Preference is given to using hydrazine, or an equivalent amount of hydrazine hydrate, in at least equimolar amount or in excess, where a relatively large excess, for example more than 20 mol %, based on 1 mol of β-keto ester II, is generally not required. Preference is given to using 1.01 to 1.1 mol, in particular about 1.05 mol, of hydrazine per mole of compound II.

The reaction of II with hydrazine is preferably carried out in an organic solvent. Examples of suitable organic solvents are protic polar solvents, for example aliphatic alcohols having preferably 1 to 4 carbon atoms, such as methanol, ethanol, n-propanol, isopropanol, n-butanol, isobutanol or tert-butanol, aromatic hydrocarbons, such as benzene, toluene, xylenes, cumene, chlorobenzene, nitrobenzene or tert-butylbenzene, aprotic polar solvents, for example cyclic or acyclic ethers, such as diethyl ether, tert-butylmethyl ether (MTBE), tetrahydrofuran (THF) or dioxane, cyclic or acyclic amides, such as dimethylformamide, dimethylacetamide, N-methylpyrrolidone or tetramethylurea, and also mixtures of the solvents mentioned above. The reaction is preferably carried out in a protic polar solvent, in particular in a $C_1$–$C_4$-alkanol and particularly preferably in ethanol.

The reaction is preferably carried out at temperatures above 0° C., in particular at at least 10° C. and particularly preferably at at least 15° C. In general, the upper temperature limit is the boiling point of the solvent in question if the reaction is carried out under atmospheric pressure. Preferably, a reaction temperature of 100° C., in particular 60° C. and particularly preferably 40° C. is not exceeded. For practical reasons, the reaction is frequently carried out at room temperature.

Depending on the reactivity of the ester II and the reaction temperature, the reaction time required for complete conversion is in the range from 1 h to 48 h and preferably in the range from 10 to 15 h.

Work-up of the reaction mixture and isolation of the hydroxypyrazole III (or its tautomer IIIa) are carried out in a customary manner by removing the solvent, for example by extraction, distillation or filtration. Further purification can take place, for example, by crystallization or chromatographically. However, the product is frequently obtained in a purity which does not require further purification steps. This is true in particular when protic polar solvents are used. In these solvents, the hydroxypyrazoles III are generally poorly soluble, if at all, and they crystallize from the reaction solution in a form which is sufficiently pure to allow isolation by filtration. Step 1 of the process according to the invention affords the hydroxypyrazoles III in good to very good yields of generally at least 60%.

In the process according to the invention, the preparation of the hydroxypyrazole III is followed by an alkylation step to introduce the substituent $R^1$ and the introduction of the difluoromethyl group.

The reaction of the hydroxypyrazole III in variant A or the difluoromethoxypyrazole VI in variant B with the alkylating agent $R^1$-L is preferably carried out in an aprotic organic solvent, for example one of the aromatic hydrocarbons mentioned in step 1, a cyclic or acyclic ether or a cyclic or acyclic amide, or mixtures of these solvents. Preference is given to aromatic hydrocarbons and in particular alkylaromatic compounds such as xylene and toluene.

The alkylating agents $R^1$-L are preferably selected from the group consisting of $C_1$–$C_4$-alkyl chlorides, $C_1$–$C_4$-alkyl bromides, $C_1$–$C_4$-alkyl iodides and, in particular, di-$C_1$–$C_4$-alkyl sulfates, and particular preference is given to the respective primary alkyl compounds and in particular the methyl compounds. A very particularly preferred alkylating agent $R^1$-L is dimethyl sulfate.

In general, the alkylating agent $R^1$-L is employed in an at least equimolar amount, preferably not more than 2 mol, in particular not more than 1.6 mol, per mole of the pyrazole III or VI in question. With particular preference, the alkylating agent $R^1$-L is, in variant A, employed in an amount of from 1.4 to 1.6 mol per mole of the compound III and, in variant B, in an amount of from 1.0 to 1.3 mol per mole of compound VI.

The reaction of the pyrazoles III or VI with $R^1$-L can be carried out in the absence or presence of an auxiliary base. The reaction of III with $R^1$-L is preferably carried out in the presence of an auxiliary base, and the reaction of VI with $R^1$-L is preferably carried out in the absence of an auxiliary base.

Suitable auxiliary bases are alkali metal and alkaline earth metal hydroxides, for example sodium hydroxide, potassium hydroxide or calcium hydroxide, and also, preferably, alkali metal and alkaline earth metal carbonates, in particular sodium carbonate or potassium carbonate. The auxiliary base is preferably employed in a substoichiometric amount (calculated as base equivalents), preferably in an amount of from 0.3 to 0.5 equivalents, based on the pyrazole III or VI in question.

The reaction of III or VI with $R^1$-L is generally carried out at temperatures of at least 0° C. up to the boiling point of the solvent in question, preferably in the range from 20° C. to 120° C. and in particular in the range from 70° C. to 120° C.

The required reaction time is generally in the range from 0.5 h to 12 h and preferably in the range from 1 to 6 h.

In general, following the reaction, ammonia, an ammonium salt such as ammonium chloride or ammonium sulfate or an aliphatic or cycloaliphatic amine is added to the reaction mixture to destroy excess alkylating agent $R^1$-L. It is also possible to treat the reaction mixture with an alkali metal hydroxide, preferably in the form of an aqueous solution. Frequently, the alkylating agent is destroyed using aqueous ammonia solution or a primary or secondary aliphatic or cycloaliphatic amine, for example diethylamine. In the case of relatively volatile compounds such as alkyl chlorides, bromides and iodides, it may not be necessary to destroy the alkylating agent.

Work-up of the reaction mixture and isolation of the N-alkylated pyrazoles IV or I is carried out in a customary manner by removing the solvent, for example by extraction, distillation or filtration. Further purification can be carried out, for example, by crystallization or chromatographically.

Surprisingly, the alkylation of III in variant A takes place with considerably higher selectivity for the formation of IV as compared to its isomer V, for example 4:1 and better, compared to the reaction of II with alkylhydrazines, so that it is possible to isolate the compound IV in a relatively uncomplicated manner from the crude product. IV, for example, can be isolated by acidifying the reaction mixture, preferably to a pH of <2, for example pH=1. As a result, the compound IV precipitates as a solid from the reaction solution. This solid can then be purified, for example by crystallization from an organic solvent, preferably from a polar organic solvent which is at least partially miscible with water, such as methanol, ethanol, ethers, for example THF, MTBE or dioxane, and amides, for example DMF, DMAA or NMP, particular preference being given to mixtures of these solvents with water, especially to aqueous ethanol. Moreover, the yields of IV, based on II, obtainable by variant A according to the invention are considerably higher than in the reaction of II with alkylhydrazines. Furthermore, the use of expensive alkylhydrazine is avoided.

The alkylation of VI according to variant B, in turn, affords the compound I in particularly good yields and with high selectivity, with the formation of only negligible amounts of the undesired isomer 5-aryl-1-alkyl-3-difluoromethoxypyrazole of the formula.

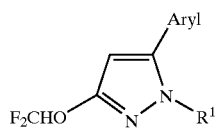

In principle, the reaction of III or IV with chlorodifluoromethane has already been disclosed in the publications mentioned at the outset. In this respect, these publications are incorporated herein by way of reference.

The reaction of III or IV is generally carried out by adding, for example as a gas, an at least equivalent amount of chlorodifluoromethane to the reaction mixture. Preferably, an excess of chlorodifluoromethane is used. In general, it is not required to use an excess of more than 10 mol per mole of III or IV. Preference is given to using from 3 to 7 mol of chlorodifluoromethane. In variant A, an excess of 8 mol, in particular 6 mol, of chlorodifluoromethane per mole of pyrazole IV is preferably not exceeded.

In principle, it has been found to be advantageous to carry out the reaction of III or IV with chlorodifluoromethane in the presence of a base. Suitable auxiliary bases are organic, preferably aliphatic or cycloaliphatic, amines, such as diethylamine, triethylamine, cyclohexylamine and the like, alkali metal and alkaline earth metal hydroxides, for example sodium hydroxide, potassium hydroxide or calcium hydroxide, alkali metal and alkaline earth metal carbonates, such as sodium carbonate or potassium carbonate, and also alkali metal alkoxides, such as sodium methoxide or potassium methoxide or sodium ethoxide or potassium ethoxide. Particularly preferred bases are alkali metal hydroxides, in particular sodium hydroxide and potassium hydroxide. The auxiliary base is preferably employed in an at least equimolar amount (calculated as base equivalents), preferably in excess, for example in an amount of from 1.5 to 2.0 mol, based on the pyrazole III or IV in question. The difluoromethylation of III (variant B) is preferably carried out at a controlled pH of at least 8, for example in the range from pH 8 to pH 12–13.

In general, reactions with chlorodifluoromethane are carried out in an organic solvent, preference being given to polar organic solvents which are preferably at least partially water-miscible, such as ethers, for example, THF, MTBE or dioxane, and amides, for example DMF, DMAA or NMP, and mixtures of these solvents with water. Particular preference is given to mixtures of at least 70% by volume and up to 99% by volume, in particular 85–95% by volume, of cyclic ether and 5–15% by volume of water, and to the abovementioned amides.

The reaction is preferably carried out at temperatures above 40° C., in particular at least 60° C. and particularly preferably in the range from 70° C. to 90° C.

Work-up of the reaction mixture and isolation of the difluoromethylated pyrazoles I or VI is carried out in a customary manner by removing the solvent, for example by extraction, distillation or filtration. Further purification can be carried out, for example, by crystallization or chromatographically.

The process according to the invention is particularly suitable for preparing compounds where $R^1$=methyl.

Aryl is preferably phenyl which has one, two, three or four, preferably 2 or 3, of the abovementioned substituents, where 2 substituents attached to adjacent carbon atoms may also form a 3-, 4- or 5-membered saturated or unsaturated chain. The chain may also include one or two heteroatoms, for example nitrogen, sulfur or oxygen, and/or one or two carbonyl or thiocarbonyl functions, as chain members.

Preferred substituents are halogen, $C_1$–$C_4$-alkyl, which may be unsubstituted or substituted by halogen, phenyl or a $C_1$–$C_4$-alkoxy group, alkenyl, alkynyl, $NO_2$, a group $COOR^5$ or a group $OR^6$, where $R^5$ and $R^6$ independently of one another are selected from the group consisting of hydrogen, $C_1$–$C_4$-alkyl, $C_3$–$C_4$-alkenyl, $C_3$–$C_4$-alkynyl, $C_1$–$C_4$-alkoxy-$C_1$–$C_4$-alkyl and $C_1$–$C_4$-alkoxycarbonyl-$C_1$–$C_4$-alkyl. The process is particularly suitable for preparing compounds I in which aryl is a group of the formula

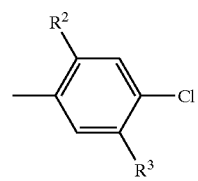

in which $R^2$ and $R^3$ independently of one another are hydrogen or one of the abovementioned substituents and, in particular, have the following meanings:

$R^2$ is hydrogen, in particular fluorine or chlorine,
$R^3$ is hydrogen, $C_1$–$C_4$-alkyl, $NO_2$, $COOR^5$ or $OR^6$, where $R^5$ and $R^6$ independently of one another are hydrogen, $C_1$–$C_4$-alkyl, $C_3$–$C_4$-alkenyl, $C_3$–$C_4$-alkynyl, $C_1$–$C_4$-alkoxy-$C_1$–$C_4$-alkyl or $C_1$–$C_4$-alkoxycarbonyl-$C_1$–$C_4$-alkyl.

$R^3$ is preferably hydrogen or a group $OR^6$. $R^6$ is preferably $C_1$–$C_4$-alkyl, $C_3$–$C_4$-alkynyl, $C_1$–$C_4$-alkoxycarbonyl-$C_1$–$C_4$-alkyl. $R^3$ is in particular hydrogen.

The compounds of the formula VIa

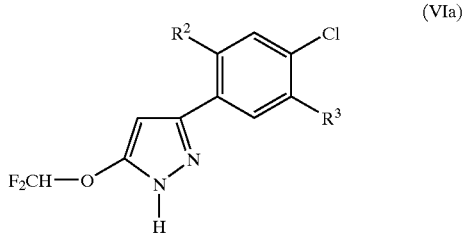

obtained as intermediates in variant B of the process according to the invention, in which $R^2$ and $R^3$ have the meanings given above, are novel and also form part of the subject matter of the present invention.

The examples below serve to illustrate the invention; they are not to be understood as imposing any limitations, however.

The starting material used in the examples below was methyl 3-(2,4-dichlorophenyl)-3-oxopropionate or ethyl 3-(4-chloro-2-fluorophenyl)-3-oxopropionate, obtainable by basic condensation of the corresponding 2,4-dihaloacetophenones with dimethyl carbonate and diethyl carbonate, respectively.

EXAMPLE 1

3-(4-Chloro-2-fluorophenyl)-5-difluoromethoxy-1-methyl-1H-pyrazole (Variant B)

1.1 3-(4-Chloro-2-fluorophenyl)-5-hydroxy-1H-pyrazole 428.4 g of ethyl 3-(4-chloro-2-fluorophenyl)-3-oxopropionate were initially charged in 1400 ml of ethanol. Over a period of 15 min, 92 g of hydrazine hydrate were added dropwise, the mixture was stirred at room temperature overnight, the precipitated solid was filtered off and the filtrate was concentrated to ⅓ of its original volume. The mixture was stirred for another two nights, the resulting solid was filtered off with suction and the filtrate was again concentrated to ⅓ of its original volume. This gave a total of 289.1 g (77.7%) of 3-(4-chloro-2-fluorophenyl)-5-hydroxy-1H-pyrazole as a colorless solid. M.p.: 194° C.

$^1$H-NMR (DMSO-d6, TMS): δ 5.88 (s, 1H), 7.35 (dd, 1H), 7.52 (dd, 1H), 7.83 (t, 1H), 9.0–11.2 (br), 11.2–13.0 (br).

1.2 3-(4-Chloro-2-fluorophenyl)-5-difluoromethoxy-1H-pyrazole 64 g of the 3-(4-chloro-2-fluorophenyl)-5-hydroxy-1H-pyrazole obtained in step 1.1 were initially charged in 600 ml of dioxane. A solution of 24 g of sodium hydroxide in 70 ml of water was added, and the mixture was heated at reflux. With stirring, 238.7 g (2.76 mol, 9.2 eq.) of gaseous chlorodifluoromethane were added, and during the addition the pH was monitored constantly and, when it approached the neutral range (pH<9), increased by addition of additional NaOH solution to about pH 12. After 6 h, the mixture was allowed to cool, 1800 ml of water were added and the mixture was extracted twice with in each case 500 ml of MTBE. The combined organic phases were washed with in each case 500 ml of water and saturated sodium chloride solution, dried over $Na_2SO_4$, filtered and concentrated. This gave 58.7 g of crude 3-(4-chloro-2-fluorophenyl)-5-difluoromethoxy-1H-pyrazole. 32.3 g of this mixture were distilled under reduced pressure, giving 11.6 g of the title compound as an oil of a purity of 86%. Yield: 22.9%

$^1$H-NMR (DMSO-d6, TMS): δ 6.32 (d, 1H), 7.14 (t, 1H), 7.32 (dd, 2H), 7.39 (dd, 1H), 7.81 (t, 1H), 12.9 (s, 1H)

1.3 3-(4-Chloro-2-fluorophenyl)-5-difluoromethoxy-1-methyl-1H-pyrazole 11.6 g of the 3-(4-chloro-2-fluorophenyl)-5-difluoromethoxy-1H-pyrazole (purity 86%) obtained in step 1.2 were initially charged in 100 ml of toluene. 6.2 g of dimethyl sulfate were added dropwise, and the mixture was heated at reflux for 3 h. After cooling, 25 ml of saturated aqueous $NH_4Cl$ solution were added, the mixture was stirred for 1 h and the organic phase was separated off and washed with water until neutral. Drying over $Na_2SO_4$ and concentration gave 11.3 g of 3-(4-chloro-2-fluorophenyl)-5-difluoromethoxy-1-methyl-1H-pyrazole as an oil of a purity of 82.4% (GC). Yield: 88.6%

$^1$H-NMR (DMSO-d6, TMS): δ 3.41 (s, 1H), 3.78 (s, 3H), 6.42 (d, 1H), 7.36 (dd, 1H), 7.38 (t, 1H), 7.44 (dd, 1H) 7.92 (t, 1H)

EXAMPLE 2

3-(4-Chloro-2-fluorophenyl)-5-difluoromethoxy-1-methyl-1H-pyrazole (Variant A):

2.1 3-(4-Chloro-2-fluorophenyl)-5-hydroxy-1-methyl-1H-pyrazole 50 g of 3-(4-chloro-2-fluorophenyl)-5-hydroxy-1H-pyrazole from Example 1.1 were initially charged in 1500 ml of toluene. 35.5 g of dimethyl sulfate were then added, and the mixture was heated at reflux for 3 h. After cooling to room temperature, the mixture was made alkaline using ammonia, stirred overnight and acidified by addition of hydrochloric acid. The mixture was then cooled to 0° C., and the precipitated solid was filtered off. After drying, 49.4 g of 3-(4-chloro-2-fluorophenyl)-5-hydroxy-1-methyl-1H-pyrazole were obtained as crude product (purity according to NMR about 80%, impurity essentially starting material), which was purified by recrystallization from toluene to >95% purity. Yield 49.4 g, 74.1%. M.p.: 204° C.

$^1$H-NMR (DMSO-d6, TMS): δ 3.65 (s, 3H), 5.92 (d, 1H), 7.35 (d, 1H), 7.52 (d, 2H), 7.94 (t, 1H)

2.2 3-(4-Chloro-2-fluorophenyl)-5-difluoromethoxy-1-methyl-1H-pyrazole 57.1 g of 3-(4-chloro-2-fluorophenyl)-5-hydroxy-1-methyl-1H-pyrazole from Example 2.1 were initially charged in 500 ml of dioxane. A solution of 18.8 g of NaOH in 50 ml of $H_2O$ was added, the mixture was heated at reflux and 85 g (0.98 mol=3.9 eq.) of gaseous chlorodifluoromethane were introduced. The mixture was poured into 1.5 l of water and extracted twice with 500 ml of MTBE, and the combined organic phases were extracted once with 500 ml of water and once with 500 ml of saturated sodium chloride solution. Drying and concentration of the organic phase gave 57.6 g of 53% pure 3-(4-chloro-2-fluorophenyl)-

5-difluoromethoxy-1-methyl-1H-pyrazole as an oil which was purified further by vacuum distillation. This gave the title compound in a purity of 94% in a yield of 43.8%.

COMPARATIVE EXAMPLE 1

Preparation of 3-(4-chloro-2-fluorophenyl)-5-hydroxy-1-methyl-1H-pyrazole using methylhydrazine 1000 g of ethyl 3-(4-chloro-2-fluorophenyl)-3-oxopropionate were initially charged in 2500 ml of diethylene glycol dimethyl ether, and 650 g of methylhydrazine (35% in $H_2O$) were added dropwise. The reaction mixture was heated at reflux for 2 h, allowed to cooled and poured into a mixture of 5 l of water and 300 ml of ethyl acetate. Further portions of ethyl acetate were added to the resulting slimy precipitate until a crystalline material was formed which was then filtered off. The product obtained after drying under reduced pressure contained the title compound in a mixture with the isomeric 5-(4-chloro-2-fluorophenyl)-3-hydroxy-1-methyl-1H-pyrazole in a molar ratio of 2.5:1. Crystallization from ethyl acetate/ethanol (7:3 v/v) gave 209 g of the title compound in a purity of about 98% (yield 22.5%).

EXAMPLE 3

3-(2,4-Dichlorophenyl)-5-difluoromethoxy-1-methyl-1H-pyrazole (Variant B)

3.1 3-(2,4-Dichlorophenyl)-5-hydroxy-1H-pyrazole 970 g of methyl 3-(2,4-dichlorophenyl)-3-oxopropionate were initially charged in 4000 ml of ethanol. Over a period of 15 min, 201 g of hydrazine hydrate were added dropwise, the mixture was stirred at room temperature overnight, the precipitated solid was filtered off and the filtrate was concentrated to ⅓ of its original volume. The filtrate was stirred for another two nights, the resulting solid was filtered off with suction and the filtrate was again concentrated to ⅓ of its original volume. This gave a total of 714.2 g (79.4%) of 3-(2,4-dichlorophenyl)-5-hydroxy-1H-pyrazole as a colorless solid. M.p.: 198° C.

$^1$H-NMR (DMSO-d6, TMS): δ 5.92 (s, 1H), 7.50 (d, 1H), 7.6–7.8 (m, 2H), 11.6–12.6 (br)

3.2 3-(2,4-Dichlorophenyl)-5-difluoromethoxy-1H-pyrazole 237 g of 3-(2,4-dichlorophenyl)-5-hydroxy-1H-pyrazol from Example 3.1 were initially charged in 2160 ml of dioxane. A solution of 84 g of sodium hydroxide in 250 ml of water was added, and the mixture was heated at reflux. With stirring, 620 g (7.17 mol, 6.9 eq.) of gaseous chlorodifluoromethane were introduced, and, during the addition, the pH was monitored continuously and when it approached the neutral range (pH 9) increased to pH 12 by addition of additional NaOH solution. After 6 h, the mixture was allowed to cool, 1.7 l of water were added and the mixture was extracted three times with in each case 500 ml of MTBE. The combined organic phases were washed with in each case 1500 ml of water and saturated sodium chloride solution, dried over $Na_2SO_4$, filtered and concentrated. The residue was suspended in 500 ml of cyclohexane and heated to reflux, and undissolved particles were filtered off. The residue was once more extracted with 200 ml of boiling cyclohexane. The combined filtrates were concentrated to obtain the title compound. This gave 136.7 g of 3-(2,4-dichlorophenyl)-5-difluoromethoxy-1H-pyrazole as a solid. (Yield 47.3%).

$^1$H-NMR (DMSO-d6, TMS): δ 6.42 (s, 1H), 7.35 (t, 1H), 7.57 (dd, 1H), 7.63 (d, 1H), 7.78 (d, 2H), 13.8–14.2 (br)

3.3 3-(2,4-Dichlorophenyl)-5-difluoromethoxy-1-methyl-1H-pyrazole 457.2 g of 3-(2,4-dichlorophenyl)-5-difluoromethoxy-1H-pyrazole from Example 3.2 were initially charged in 2300 ml of toluene. 227.3 g of dimethyl sulfate were added dropwise, and the mixture was heated at reflux for 3 h. After cooling, 500 ml of saturated aqueous $NH_4Cl$ solution were added, the mixture was stirred for 1 h and the organic phase was separated off and washed with water until neutral. Drying over $Na_2SO_4$ and concentration gave 377.8 g of 3-(2,4-dichlorophenyl)-5-difluoromethoxy-1-methyl-1H-pyrazole of a purity of 92.9% (GC). Yield: 73.1%. M.p.: 35° C.

$^1$H-NMR (CDCl$_3$, TMS): δ 3.78 (s, 3H), 6.41 (s, 1H), 6.58 (t, 1H), 7.26 (dd, 1H), 7.42 (d, 1H), 7.72 (d, 1H)

EXAMPLE 4

3-(2,4-Dichlorophenyl)-5-difluoromethoxy-1-methyl-1H-pyrazole (Variant A)

4.1 3-(2,4-Dichlorophenyl)-5-hydroxy-1-methyl-1H-pyrazole 30 g of 3-(2,4-dichlorophenyl)-5-hydroxy-1H-pyrazole from Example 3.1 were initially charged in 750 ml of toluene. 23.1 g of dimethyl sulfate and 7.5 g of potassium carbonate were added, and the mixture was heated at reflux for 2 h. After cooling to room temperature, the mixture was made alkaline using ammonia and stirred overnight. The mixture was acidified by addition of hydrochloric acid (pH about 1) and cooled to room temperature, and the precipitated solid was filtered off. Drying gave 21.4 g of 3-(2,4-dichlorophenyl)-5-hydroxy-1-methyl-1H-pyrazole (purity according to GC 99.2%, yield 66.8%). M.p.: 128° C.

$^1$H-NMR (DMSO-d6, TMS): δ 3.59 (s, 3H), 5.92 (s, 1H), 7.42 (dd, 1H), 7.61 (d, 1H), 7.80 (d, 1H), 11.2 (s, 1H)

4.2 3-(2,4-Dichlorophenyl)-5-difluoromethoxy-1-methyl-1H-pyrazole 9 g of 3-(2,4-dichlorophenyl)-5-hydroxy-1-methyl-1H-pyrazole from Example 4.1 were initially charged in 50 ml of dimethylacetamide, and 5.4 g of potassium carbonate were added. The mixture was heated at 90° C., and 48 g of gaseous chlorodifluoromethane were introduced over a period of 1 h. The mixture was poured into 800 ml of water and extracted twice with 300 ml of MTBE, and the combined organic phases were extracted once with 100 ml of water and once with 100 ml of saturated sodium chloride solution. Drying and concentration of the organic phase gave 10.2 g of 3-(2,4-dichlorophenyl)-5-difluoromethoxy-1-methyl-1H-pyrazole of a purity of 56% (yield 50.2%, based on the title compound), which was purified further by vacuum distillation.

COMPARATIVE EXAMPLE 2

Preparation of 3-(2,4-dichlorophenyl)-5-hydroxy-1-methyl-1H-pyrazole using methylhydrazine 1980 g of methyl 3-(2,4-dichlorophenyl)-3-oxopropionate were initially charged in 3000 ml of diethylene glycol dimethyl ether. Over a period of 30 min, 728 g of methylhydrazine (51% in $H_2O$) were added dropwise, and the mixture was heated at reflux for 2.5 h. After cooling, the reaction mixture was poured into a mixture of 6 l of water and 600 ml of ethyl acetate, and the precipitated solid was filtered off with suction. The solid was recrystallized from ethyl acetate/ethanol (7:3 v/v) and dried under reduced pressure. This gave 894 g of an about 80% pure mixture of 3-(2,4-dichlorophenyl)-5-hydroxy-1-methyl-1H-pyrazole and 5-(2,4-dichlorophenyl)-3-hydroxy-1-methyl-1H-pyrazole in a molar ratio of 3:1. Repeated fractional recrystallization from ethyl acetate/ethanol (7:5 v/v) gave 444.5 g of the pure title compound (purity>98%). Yield 24.1%.

We claim:

1. A process for preparing 1-alkyl-3-aryl-5-difluoromethoxy-1H-pyrazoles of the formula I

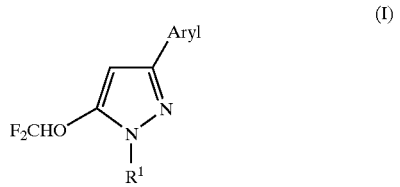

in which
Aryl is a mono- or polysubstituted phenyl ring and
$R^1$ is $C_1$–$C_4$-alkyl,
which comprises reacting, in a first reaction step, a β-keto ester of the formula II,

in which $R^a$ is $C_1$–$C_4$-alkyl and Aryl has the meanings given above with hydrazine, giving a hydroxypyrazole of the formula III

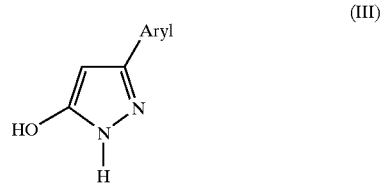

which is reacted successively with chlorodifluoromethane and an alkylating agent $R^1$-L in which $R^1$ has the meanings given above and L is a nucleophilically displaceable leaving group.

2. A process as claimed in claim 1, wherein the hydroxypyrazole III is initially reacted with a compound $R^1$-L and the resulting 1-alkyl-3-aryl-5-hydroxypyrazole IV

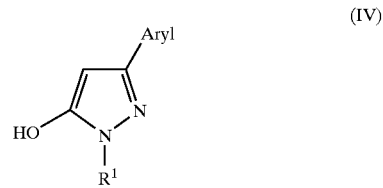

is reacted with chlorodifluoromethane.

3. A process as claimed in claim 1 or 2, wherein the reaction of the hydroxypyrazoles III or IV with chlorodifluoromethane is carried out in the presence of a base.

4. A process as claimed in claim 3, wherein the base is selected from the group consisting of alkali metal hydroxides and alkali metal carbonates.

5. A process as claimed in claim 1, wherein aryl is as defined below:

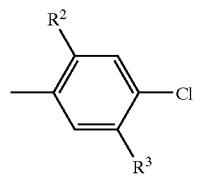

in which $R^2$ and $R^3$ have the following meanings:
$R^2$ is hydrogen, fluorine or chlorine,
$R^3$ is hydrogen, $C_1$–$C_4$-alkyl, $NO_2$, $COOR^5$ or $OR^6$, where $R^5$ and $R^6$ independently of one another are hydrogen, $C_1$–$C_4$-alkyl, $C_3$–$C_4$-alkenyl, $C_3$–$C_4$-alkynyl, $C_1$–$C_4$-alkoxy-$C_1$–$C_4$-alkyl or $C_1$–$C_4$-alkoxycarbonyl-$C_1$–$C_4$-alkyl.

6. A process as claimed in claim 1, wherein $R^1$ is methyl.

7. A process as claimed in claim 1, wherein L is selected from the group consisting of iodine, bromine, chlorine and a group $OSO_2$—$OR^1$ or $[O(R^1)_2]$r.

8. A process as claimed in claim 6, wherein the compound $R^1$-L is dimethyl sulfate.

9. A process as claimed in claim 1, wherein the reaction of compound III or IV with the alkylating agent $R^1$-L is carried out in the presence of a base.

10. A process as claimed in claim 1, wherein the alkylating agent $R^1$-L is employed in an amount of from 1 to 2 mol per mole of the compound III or IV.

11. A process as claimed in claim 1, wherein difluoromethane is used in an amount of from 3 to 10 mol per mole of compound III or IV.

* * * * *